United States Patent

Powers et al.

[11] Patent Number: 6,117,100
[45] Date of Patent: Sep. 12, 2000

[54] HEMODIALYSIS-DOUBLE DIALYZERS IN PARALLEL

[76] Inventors: Kathleen M. Powers, 1701 Tarlbark Dr., Afton, Va. 22920; Michael J. Wilkowski, 3208 Heathcote La., Keswick, Va. 22947-9160; Allen W. Helmandollar, Rte. 2, Box 649, Palmyra, Va. 22963

[21] Appl. No.: 09/092,182

[22] Filed: Jun. 5, 1998

Related U.S. Application Data

[60] Provisional application No. 60/048,968, Jun. 6, 1997.

[51] Int. Cl.[7] .......................... A61M 37/00; B01D 11/00
[52] U.S. Cl. ................................ 604/4; 210/645; 210/646
[58] Field of Search ................................ 210/321; 604/5, 604/65, 902; 422/101; 435/240; 436/526; A61M 1/16

[56] References Cited

U.S. PATENT DOCUMENTS

| | | | |
|---|---|---|---|
| 3,627,137 | 12/1971 | Bier | 210/321 |
| 3,892,664 | 7/1975 | Van Assendelft et al. | 210/321 |
| 4,353,368 | 10/1982 | Slovak et al. . | |
| 4,596,549 | 6/1986 | Minami . | |
| 4,662,871 | 5/1987 | Rafelson | 604/119 |
| 4,937,194 | 6/1990 | Pattillo et al. | 435/240 |
| 5,207,642 | 5/1993 | Orkin et al. | 604/65 |
| 5,344,568 | 9/1994 | Kitaevich et al. . | |
| 5,470,483 | 11/1995 | Bene et al. . | |
| 5,536,475 | 7/1996 | Moubayed et al. | 422/101 |
| 5,660,722 | 8/1997 | Nederlof . | |
| 5,683,640 | 11/1997 | Miller et al. . | |
| 5,691,208 | 11/1997 | Miltenyi et al. | 436/526 |
| 5,730,712 | 3/1998 | Falkval et al. | 604/5 |
| 5,744,027 | 4/1998 | Connell et al. . | |

FOREIGN PATENT DOCUMENTS 41 24 884   1/1993   Germany .

OTHER PUBLICATIONS

Kablitz, Steven et al, Pressure Control of Ultrafiltration Rate with High–Flux Dialysis Membranes, Artificial Organs 5, Feb. 1981, pp. 162–167.

*Primary Examiner*—Corrine McDermott
*Assistant Examiner*—Cheryl L Huseman
*Attorney, Agent, or Firm*—Oblon, Spivak, McClelland, Maier & Neustadt, P.C.

[57] ABSTRACT

The delivered dose of hemodialysis in large patients is often less the adequate. The present invention provides a method and apparatus for dialysis which increases the clearance of urea in patients weighing 80 kilograms or more. The apparatus is comprised of two dialyzers which may be connected to a patient in parallel configuration. The present invention can be practiced with any commercially available dialyzers and dialysis machines without requiring expensive modifications which negate manufacturers warranties and inherent safety features. The present invention provides a safe, cost effective way to increase the delivered dose of hemodialysis in patients weighing 80 kilograms or more.

3 Claims, 3 Drawing Sheets

HEMODIALYSIS-DOUBLE DIALYZERS IN PARALLEL

This is a regular national patent application which claims priority from U.S. Ser. No. 60/048,968, filed Jun. 6, 1997, (494-246-27PROV), incorporated herein by reference.

BACKGROUND OF THE INVENTION

1. Field of the Invention

The invention of this application relates to a method and apparatus for hemodialysis, and more particularly to a method and apparatus for treating patients having a large body mass.

2. Description of the Prior Art

In the field of renal dialysis, the use of dialyzer cartridges to remove blood borne-uremic toxins and by-products of metabolism has been conventional for many years. Typically, such a cartridge contains essentially two chambers separated by a semipermeable membrane. Blood is perfused through the first chamber and returned to the patient. A dialysis solution is simultaneously circulated through the second chamber. A concentration gradient is thereby established which causes toxic molecular species contained in the blood to migrate through the semipermeable membrane and into the dialysis solution.

The principle of hemodialysis has been refined extensively. Dialyzers which contain a large plurality of semipermeable hollow fiber membranes are now utilized to greatly increase the surface area, thus facilitating diffusion across the membrane. The hollow fiber membranes are composed of a variety of materials including cellulose acetate, cellulose triacetate, polyacrylonitrile, polysulfone and regenerated cellulose. These hollow fibers are small bore capillaries arranged in parallel. The bundle of fibers is typically potted in a curable sealant at both ends. Upon cure, the embedded fibers are cut through at the ends to expose the bores of the fibers, as disclosed in U.S. Pat. No. 4,227,295 (Bodnar et al.), incorporated by reference herein. The fiber bundle is then enclosed in a housing which forms the dialyzate chamber. Examples of dialyzers of this construction together with the mechanical details of closure, inlet and outlet ports, and the like are illustrated in U.S. Pat. No. 4,283,284 (Schnell) and U.S. Pat. No. 4,600,512 (Aid), both incorporated by reference herein.

In the operation of the dialyzer, patient blood is pumped through the hollow fiber bundle, and a dialysis solution is pumped through the dialyzate chamber so that dialysis solution constantly bathes the exterior hollow fiber surfaces. Pump assisted movement of blood through the dialyzer is required in order to displace a sufficient volume for effective cleansing within a treatment time of less than six hours. Another pump propels dialysis solution through the dialyzate chamber and also regulates, by valves under microprocessor control, the proper mixing of dialysis solution concentrate and water. Electrolyte concentrations are monitored by continuous conductivity measurement. Another function of this pumping device is to carefully control fluid back pressure so as to prevent excessive water loss from the blood. Examples of such units are disclosed in U.S. Pat. Nos. 4,137,168, 5,344,568, and 5,744,027, all of which are incorporated by reference herein.

One measure of adequacy of dialysis for the individual patient as to a particular dialyzer is calculated using Daugirdas' equation:

$$Kt/V \geq 0.8$$

wherein V is an expression of the volume of distribution of urea which is approximately equal to total body fluid volume derived for each individual patient from data such as height, weight, and sex, K is the urea clearance of the dialyzer in use, in ml of blood totally cleared in urea each minute, and t is the treatment time. A typical product insert accompanying a dialyzer unit contains a graph of urea clearance versus blood flow rate obtained by random testing of a sample of dialyzers from a particular manufacturing lot. Upon incorporating these values into the above equation, the minimum treatment time can be calculated for a given Kt/V value. Other parameters that may be varied to achieve adequate dialysis include blood flow rate (BFR), dialysis solution flow rate (DFR), dialyzer competency, and temperature.

It has been determined empirically that Kt/V values of about 0.8 or greater are associated with low levels of morbidity. See Gotch, L. A., Sargent, J. A., *Kidney Int.*, 28:526–537, 1985. Even in the use of new dialyzer units there is some risk that a unit selected from a particular lot will have a significantly lower K value than the value depicted by the product insert graph. The patient receiving treatment from such a unit is therefore at risk of being under dialyzed. The likelihood of under-dialysis increases upon reuse of the dialyzer because of the unpredictability of loss of dialyzer competence.

Dialysis adequacy in patients weighing greater than 81 kg. has been identified as an area that needs to be explored. The delivered dose of hemodialysis in large patients with end stage renal disease (ESRD), as measured by urea reduction ratio (URR) and urea clearance normalized for the volume of distribution of urea (Kt/V(urea)), is often less than adequate. See Carroll CE, et al., "Patient Factors Associated with Delivered KT/V in the U.S.", *J Am Soc Nephrol* 6:594, 1995. The 1995 ESRD Core Indicators project found statistically significant differences in urea reduction ratio (URR) in patients with a mean body weight of 81 kg. or greater. Current dialysis modalities do not take into account the growing number of patients fitting into this category. Use of large surface area dialyzers, high blood flow rates, high dialyzate flow rates and increased dialysis time are maneuvers that can increase the delivered dose of hemodialysis. Despite optimization of these parameters, patients weighing greater than 80 kg are still at risk of receiving less than adequate doses of hemodialysis, resulting in fatigue, tingling of extremities and changes in skin color of the patient.

It is known from the article by V. Albertini, et al., "Serial and Parallel Pairs of Dialyzers for High-Efficiency Treatment", in *Kidney International* 31(1), page 247, 1987, to arrange serially or in parallel two blood purifiers to enhance the purifying action. A means for precisely regulating and monitoring the filtrate and substituate flow is not mentioned in this publication. A recent report of two F-80 dialyzers used in series has demonstrated increased urea clearance when used in a system for hemodiaffiltration. See Bosch JP, et al., "Hemodialysis High Efficiency Treatments: Six Year Outcomes", *J. Am. Soc. Nephrol.* 6:484, 1995. However, such systems require machine alterations which would negate the warranty and some of the inherent safety features.

U.S. Pat. No. 5,660,772 also discloses a hemodiafiltration apparatus with two blood filters connected in series. However, this system requires a pump between the first and second blood filters.

SUMMARY OF THE INVENTION

It is therefore an object of the present invention to provide an apparatus and method for high efficiency hemodialysis of larger patients, i.e., those weighing more than 80 kg that can be used in all dialysis centers as opposed to only those which have advanced machine technicians.

It is also an object of the invention to be able to practice the invention with any commercially available dialyzers without having to make modifications thereto which would negate the manufacturers' warranty and some of the inherent safety features.

It is also an object of the invention to provide increased dialysis to patients with a large volume of urea distribution without increasing the incidence of dialyzer clotting episodes and while also minimizing costs.

These objects are achieved through the use of two dialyzers which are inserted into a hemodialysis circuit in parallel.

Use of the double dialyzer in a parallel configuration achieved an increment in delivered dialysis dose. Any increase may be particularly important in patients who have a high volume of distribution of urea. Such patients are at risk for receiving a less than optimal dialysis dose despite maximizing blood flow rates and dialyzate flow rates, surface area of the artificial kidney and dialysis time.

Although the percentage and absolute increases in clearance achieved using the double dialyzers in parallel seem small, they are clinically significant. Recent United States Renal Data System analysis has shown that a 0.1 increase in Kt/V is associated with a substantially decreased adjusted relative risk of death from cardiac, cerebrovascular and infectious diseases. See Bloembergen WE, et al., "Relationship of Dose of Hemodialysis and Cause-Specific Mortality", *Kidney International,* 50:557–565, 1996. The clinical effect of an increased Kt/V may be even more beneficial for patients with a less than adequate Kt/V(<1.2) who are brought up to 1.2 to 1.4. See Gotch FA, et al., "Clinical Outcome Relative to the Dose of Dialysis is Not What You Think; the Fallacy of the Mean", *American Journal of Kidney Diseases,* 30:1–15, 1997.

In patients who are greater than 80 kg body weight, a Kt/V of >1.2 may be difficult to achieve because of their large volume of distribution of urea. See Ifudu O, et al., "Standardized Hemodialysis Prescriptions Promote Inadequate Treatment in Patients with Large Body Mass", *Annals Intern Med.,* 128:451–454, 1998. The present invention increases clearance after other important parameters such as blood flow rate, dialysate flow rate, artificial kidney size and time on dialysis have been optimized.

A major advantage of the two dialyzers in parallel according to this invention, is that all the standard safety features on the Fresinius 2008E and other commercially available dialysis machines are utilized and do not have to be adjusted or bypassed.

One advantage of the present system compared to a system comprised of two dialyzers in series is that if one of the dialyzers becomes clotted the patient can continue to run on the remaining dialyzer and changes in heparinization may be made prior to the next run.

Although the present invention has been described in connection with a Fresinius 2008E dialysis machine and two Fresinius F-80 dialyzers, it will be readily apparent to those skilled in the art that other known dialysis machines and dialyzers may also be used to practice the present invention.

The invention described herein can be practiced with any hollow fiber dialyzer. Dialyzers of this type are comprised of a tubular shaped shell which is separated into two compartments by a semipermeable membrane. The shell has four ports, two of which communicate with a blood compartment and two with a dialyzate compartment. The boundary between the two compartments is maximized by using a membrane divided into multiple hollow fibers or capillaries. An example of such a dialyzer is the Fresinius F-80, a high flux dialyzer which has a polysulfone membrane and a surface area of 2.1 m$^2$.

Examples of other suitable dialyzers and dialysis machines along with their manufacturer's specifications can be found in Daugirdas' *Handbook of Dialysis.*

DETAILED DESCRIPTION OF THE INVENTION

The apparatus according to the present invention comprises:

(a) two dialyzers in parallel, each of which is divided into two compartments by a semipermeable membrane;

(b) an inlet line connected to each dialyzer for conveying blood from the vascular system of a patient into the dialyzer;

(c) an outlet line connected to each dialyzer for conveying blood away from the dialyzer and back to the patient;

(d) means for pumping blood through each dialyzer and back to the patient; and (e) a dialysis solution delivery system.

Figure 1:
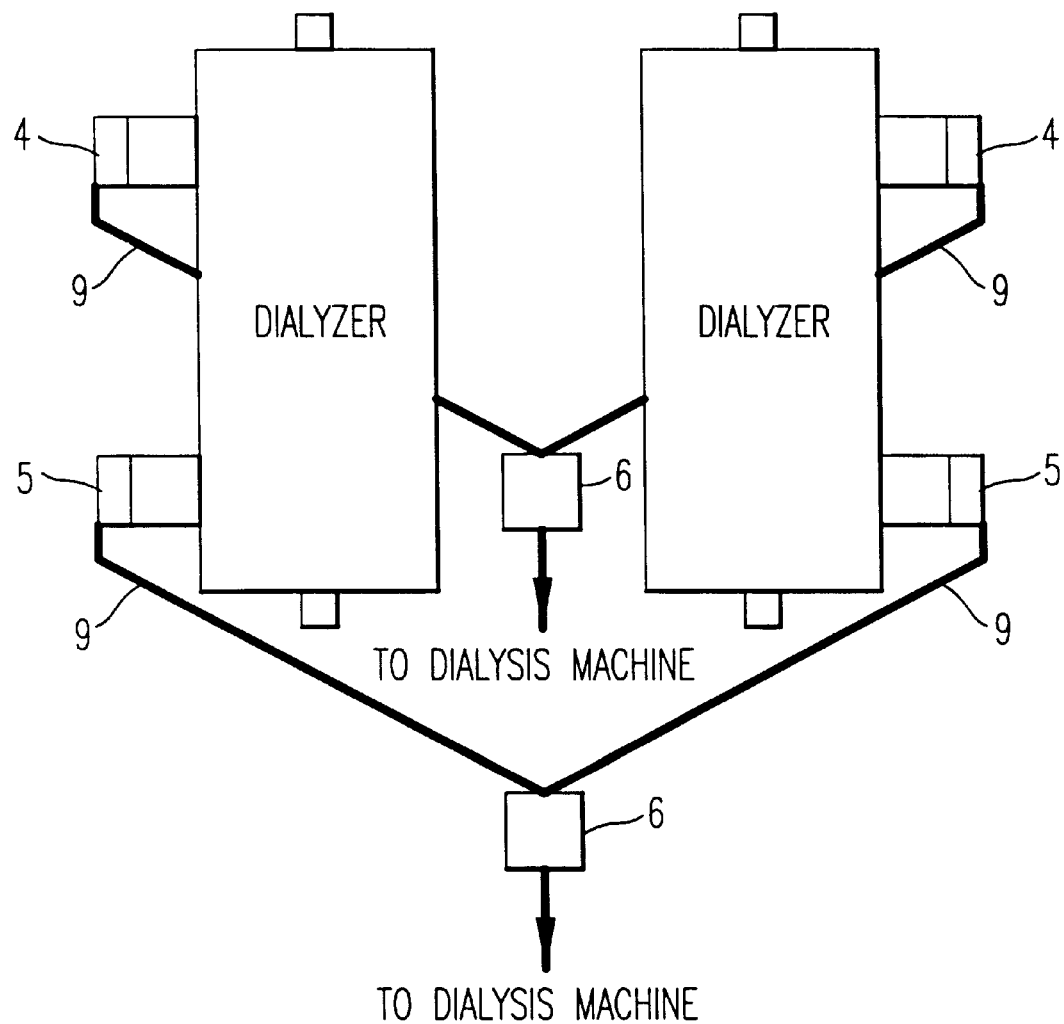
FIG. 1 is a diagram which shows the parallel set-up of the double-dialyzer system according to the present invention.
Figure 2A:
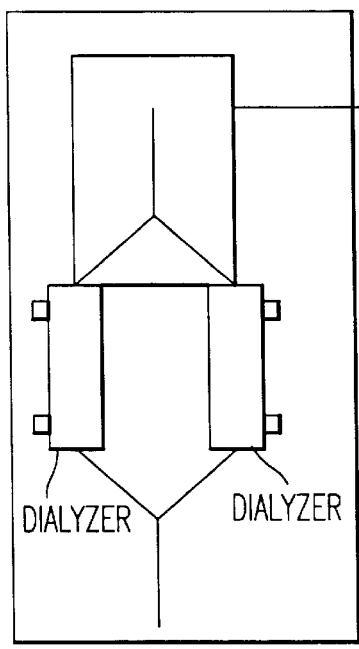
FIG. 2 is a diagram of the adapter which is used to connect the blood inlet and outlet lines to the dialyzer.
Figure 2B:
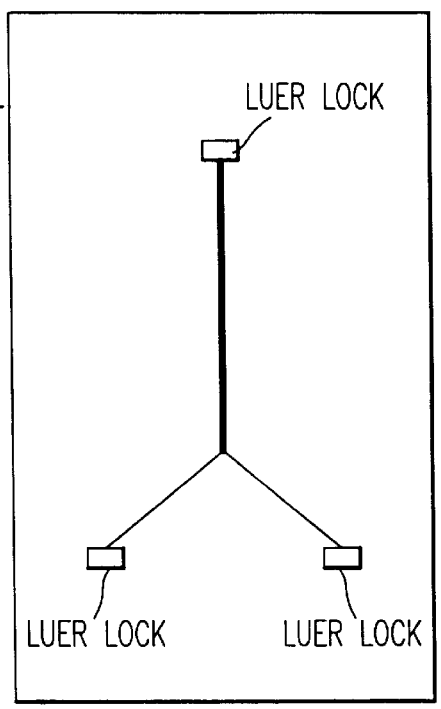

The inlet 4 and outlet 5 lines are connected to the dialyzers. Connection may be direct, or via an adapter 6. The adapter may be comprised of flexible tubing which is in the shape of a "Y" 9. The tubing has means for connecting the dialyzers to the inlet and outlet lines. The means for connecting may comprise screw-on or snap-on means. The screw-on means preferably comprises male and female luer locks (as shown in FIG. 2).

The present invention is also directed to a method for hemodialysis comprising performing hemodialysis on a patient in need thereof using the apparatus described above. The present method is preferably used to treat patients having a body weight of at least 80 kg.

The invention is also directed to an adapter for use in a dialysis apparatus, said adapter comprising means to connect a bloodline in a dialysis apparatus to two dialyzers in parallel configuration. The adapter is made of flexible tubing which is in the shape of a "Y" having a female luer lock on one end and two male luer locks on the other two ends.

The following study was conducted in order to compare the system of the present invention, two dialyzers in parallel configuration, with that of the prior art, i.e., a single dialyzer. Fourteen patients with ESRD on maintenance hemodialysis three times per week at the University of Virginia Kidney Center participated in the study. All weighed more than 80 kg and were medically stable for at least 90 days preceding the initiation of the study. All had hemodialysis vascular access (PTFE grafts) which provided a blood flow rate of 400 ml/min. All used a dialyzate flow rate of 800 ml/min. All patients were dialyzed for four hours using the Fresinius 2008E dialysis machines and Fresinius F-80 (hollow fiber, polysulfone, 2.1 m² surface area, high flux) dialyzers. All dialyzers were reprocessed using heat and citric acid with a reuse limit of fifteen.

Seven patients used the single dialyzer (control) for twelve consecutive sessions (four weeks) and seven patients used the double dialyzers (invention) in parallel for twelve consecutive sessions (four weeks) with measurement of URR and KT/V(urea) after every session. The next twelve consecutive sessions (four weeks) each group switched to the opposite dialyzer configuration and URR and KT/V (urea) were measured after each session. Patients were randomly assigned to start the study in the control or invention period. Post-dialysis urea sample was drawn from the vascular access needle 3 minutes after the cessation of dialysis. Kt/V(urea) was calculated using the formula by Daugirdas, found in *The Handbook of Dialysis:* Kt/V (urea)=−ln(R−0.008t)+(4−3.5R)UF/W, where R=postBUN/ preBUN, t=dialysis session length in hours, UF=weight loss in kilograms, W=post-dialysis weight in kilograms and BUN=blood urea nitrogen level in wt/vol. Urea removal ratio (URR) was calculated using the formula: URR= (preBUN−postBUN)/preBUN.

During the period using the invention, two Fresinius F-80 artificial kidneys were used in parallel configuration during each hemodialysis session. The two F-80 units were connected to the blood line using an adapter comprised of Y shaped tubing which has Luer locks on all three ends as shown in FIG. 2. Blood flow rates, dialyzate flow rates and time of the sessions were the same as the control period. Heparinization prescription did not change, with the double dialyzers in parallel receiving an amount of heparin as previous sessions required with adjustment as per nursing staff.

In order to measure the clearances of substances in addition to urea, iohexol, a freely dialyzable molecule (MW 821), was injected (0.25 ml/kg body weight) prior to the last dialysis session of the control and intervention periods. Pre- and post-dialysis blood sample were used to calculate an iohexol clearance(Cl(io)) using the formula: Cl(io)=[(Kt/V (io))×$V_d$(io)]/t, where Kt/V(io) was calculated using Daugirdas' formula where R=post-dialysis iohexol concentration/pre-dialysis iohexol concentration, $V_d$(io)= (166×weight in kilograms)+2490 for men or (95×weight in kilograms)+6170 for women, and t is the duration of the dialysis session in minutes. Iohexol reduction ratio was calculated as RR(io)=1−R(io).

Blood volume processed, amount of ultrafiltration and erythropoietin doses were monitored for every session. Hematocrit level was monitored each week. Patients were monitored for adequacy of heparinization, episodes of clotted dialyzers, dialyzer reactions, blood leaks and signs of bacteremia during each hemodialysis session. Means are shown +/− standard deviation. comparisons between the intervention and control measurements were made with paired two-tailed t tests; p values <0.05 were considered statistically significant. Demographic data describing the study patients are listed in Table 1.

TABLE 1

| PATIENT | AGE/GENDER (yrs) | WEIGHT (kg) | HEIGHT (cm) | DIAGNOSIS |
|---|---|---|---|---|
| 1 | 53/M | 85.5 | 177 | Diabetes |
| 2 | 52/M | 108.5 | 178 | Diabetes |
| 3 | 43/M | 166.5 | 180 | Diabetes |
| 4 | 46/F | 104 | 153 | Chronic GN |
| 5 | 66/F | 102 | 169 | Diabetes |
| 6 | 71/M | 137.5 | 188 | Diabetes |
| 7 | 58/M | 99 | 180 | Chronic GN |
| 8 | 57/M | 106.5 | 177 | Diabetes |
| 9 | 73/M | 90.5 | 177 | Hypertension |
| 10 | 58/M | 87.5 | 183 | Hypertension |
| 11 | 40/M | 80.5 | 190 | Hypertension |
| 12 | 28/M | 100 | 185 | Hereditary Nephritis |
| 13 | 70/M | 89 | 178 | Obstruction |
| 14 | 73/M | 104.5 | 190 | Diabetes |
| Mean(+/−std) | 56 | 104.4 | 179 | |

RESULTS

Figure 3:
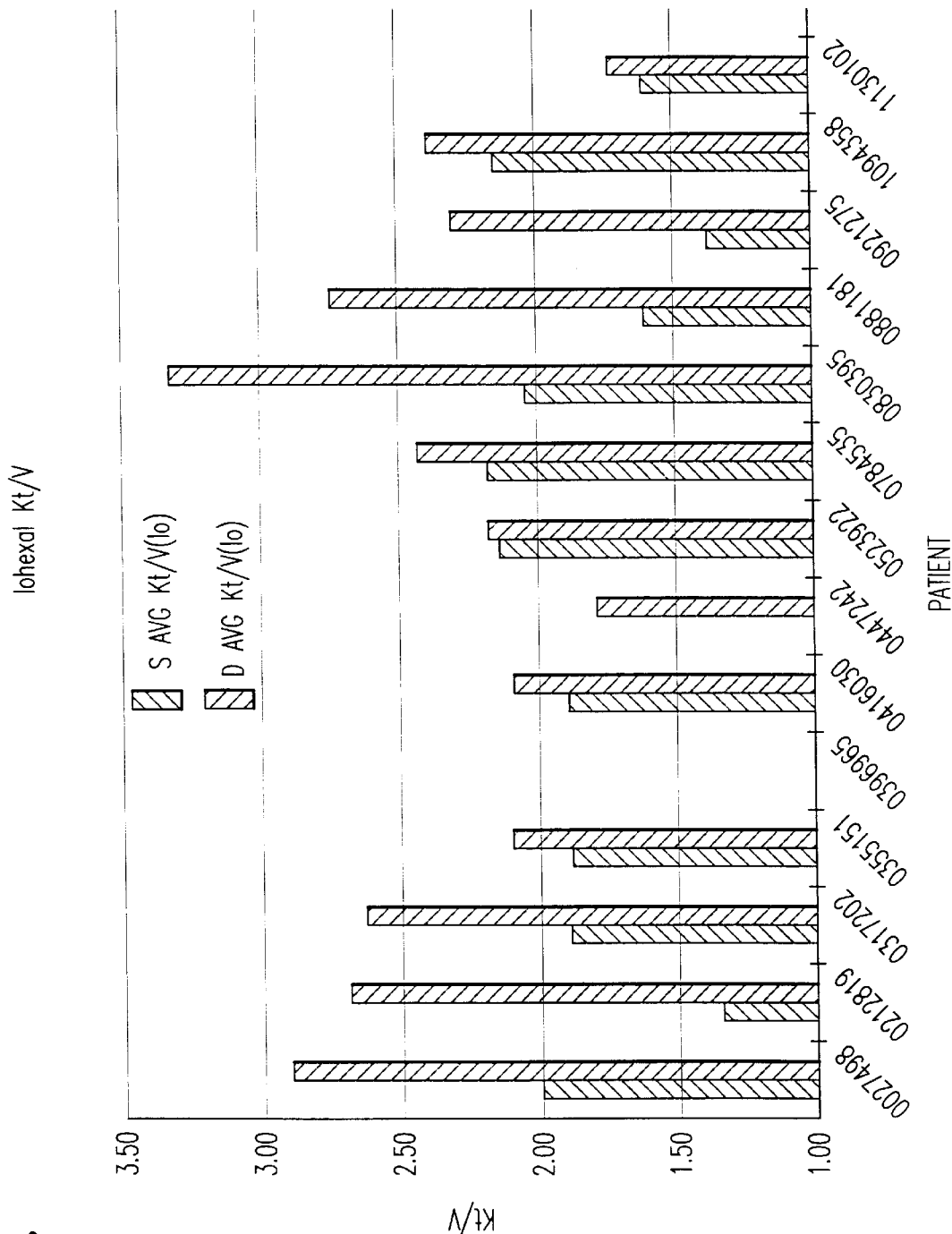
FIG. 3 shows the change in Kt/V for each patient using a single dialyzer and the double dialyzer of the invention in parallel.

A significant increase in URR and Kt/$V_{urea}$ occurred in all 14 patients during the practice of the invention compared to the control period (p<0.05). The mean URR and Kt/$V_{urea}$ for the 14 patients using the single dialyzer (control) were 0.67+/−0.32 and 1.33+/−0.28 respectively, compared to 0.72+/−0.07 and 1.53+/−0.32 for the double dialyzer in parallel (invention), as shown in Table 2. The average Kt/V increase was 0.20(15%) using the double dialyzer in parallel, while URR increased an average of 4.7 (7% change) using the double dialyzer in parallel. FIG. 3 demonstrates the change in Kt/V for each individual patient. Average volume of blood processed per session was the same in each period. The average amount of ultrafiltration required did not differ between the control and intervention sessions.

Iohexol clearance(n=12) in the intervention sessions averaged 182 ml/min+/−36.9 compared to 130 ml/min+/−25.5 in the control sessions (p<0.005), Kt/V(io) and RR(io) increased from 1.78+/−0.33 and 0.77+/−0.06 to 2.47+/− 0.540 and −0.86+/−0.05, respectively. One patient completed the invention period but received a transplant prior to the measurement of iohexol clearance at the end of the control period. One patient had an allergy to iodine and iohexol was withheld.

Data for measurement of Kt/V(urea) and URR was obtained for 301 of the 336 total session of this study (153 in the control period and 148 in the intervention period, p=NS). The exceptions included one patient who developed a clotted access while in the intervention period. This resulted in a need for a single hemodialysis session via a femoral catheter on a single dialyzer and no measurements are included from this episode. The remained of the omissions were due to inadvertent failure to obtain the post-dialysis BUN.

Adverse events during the study included one admission for volume overload and one blood leak during the control period. During the invention period one patient experienced a peri-access hematoma, one patient developed a clotted access and one patient was treated for pneumonia; None of the events required hospitalization and none could be attributed to the double dialyzer configuration. There were no dialyzer reactions, clotted dialyzers or bacteraemias during the study.

The average of the weekly hematocrits significantly differed between the control and invention periods in two patients; 32% during control and 35% during invention (p=0.038) in one patient while on 8000 units/session of erythropoietin and the second patient, on no erythropoietin, had an average weekly hematocrit of 40% during control and 38% during invention (p=0.045). In all other patients weekly hematocrit and erythropoietin dose did not differ between the control and invention period.

Heparin requirements were different in four patients. One patient required 7200 units/session on average during the control period versus 6845 units/session during the invention period (p=0.018). Three patients required more heparin per session on average during the invention period; 6450 units, 5623 units, and 5623 units versus 4133 units, 4408 units and 4538 units during the control period (p<0.05).

The average number of uses for each dialyzer was eight during this study and did not differ between the control and invention period.

Cost analysis demonstrated an increase expense of approximately $11.40 per dialysis session using the double dialyzer in parallel configuration. The cost of a new F-80 dialyzer is approximately $25.00. The usual reuse number was eight thus making the extra dialyzer cost $3.13 per session. The cost of each reprocessing of a dialyzer is $5.10. The cost of the specially manufactured connectors is $3.00 per session and they were not reused or reprocessed. Additional nursing or technician time for set up was seven minutes at an estimated cost of $0.31 per minute or $2.17 per session. The results of the study are summarized in Table 2 below.

TABLE 2

|  | Control(+/−std) | Invention(+/−std) | p-value* |
|---|---|---|---|
| URR | 0.679(0.07) | 0.72(0.07) | 0.00001 |
| Kt/V(urea) | 1.33(0.279) | 1.53(0.315) | 0.00001 |
| Iohexol Clearance | 129(25.4) | 181(36.9) | 0.000001 |
| Kt/V(iohexol) | 1.78(0.33) | 2.47(0.54) | 0.00001 |
| Reduction Ratio(iohexol) | 0.77(0.06) | 0.86(0.05) | 0.00001 |
| $V_d$(iohexol) | 17639(2890) | 17642(2508) | NS |

Abbreviations: URR = urea reduction ratio, Kt/V(Urea) = dialysis urea clearance normalized for the volume of distribution of urea, Kt/V(iohexol) = dialysis iohexol clearance normalized for the volume of distribution of iohexol, $V_d$(iohexol) = volume of distribution of iohexol, NS = not significant.
*control (single dialyzer) versus invention (double dialyzer).

In this short term study of stable hemodialysis patients with a large volume of distribution of urea, the doubling of the surface area of a biocompatible artificial kidney did not cause hemodynamic or hematologic adverse effects and increased Kt/V and URR by an average of 15%.

Having now fully described the invention, it will be apparent to one of ordinary skill in the art that many changes and modifications can be made thereto without departing from the spirit or scope of the invention as set forth herein.

What is claimed is:

1. An apparatus for use in blood dialysis comprising two dialyzers which may be connected to a patient in parallel;

(a) each said dialyzer being divided into two compartments by a semipermeable membrane; said apparatus further comprising (b) an inlet line connected to each said dialyzer for conveying blood from the vascular system of said patient into each said dialyzer;

(c) an outlet line connected to each said dialyzer for conveying blood from each said dialyzer and back to the patient;

(d) means for pumping blood through each dialyzer and back to the patient; and (e) a dialysis solution delivery system, wherein said inlet line and said outlet line are connected to said dialyzer via an adaptor comprised of flexible tubing in the shape of a "Y", said tubing comprising male and female screw on locks for connecting the dialyzers to the inlet and outlet lines.

2. A method for effecting hemodialysis on a patient, which comprises:

a) conveying blood from a patient in need of hemodialysis into an inlet line of a dialyzing apparatus; and b) returning blood to said patient through an outlet line of said dialyzing apparatus;

wherein said dialyzing apparatus is the apparatus of claim 1.

3. A method of performing dialysis on a patient, comprising:

a) selecting as the patient a human whose gross body weight is at least 80 kilograms;

b) conveying blood from the human patient into an inlet line of a dialyzing apparatus and removing uremic toxins from blood of said human patient; and c) returning the blood to said human patient through an outlet line of said dialyzing apparatus;

wherein said dialyzing apparatus is the apparatus of claim 1.

* * * * *